(12) United States Patent
Cavaf

(10) Patent No.: US 6,540,511 B1
(45) Date of Patent: Apr. 1, 2003

(54) METAL ORTHODONTIC ATTACHMENTS TREATED WITH A COATING OF THE PLATINUM GROUP METAL

(76) Inventor: Mircea Dimitri Cavaf, 18 Boul. de la Diberté, Chatillon, Hts de Seine (FR), 92320

( * ) Notice: Subject to any disclaimer, the term of this patent is extended or adjusted under 35 U.S.C. 154(b) by 0 days.

(21) Appl. No.: 09/831,208

(22) PCT Filed: Sep. 8, 2000

(86) PCT No.: PCT/FR00/02480

§ 371 (c)(1),
(2), (4) Date: May 7, 2001

(87) PCT Pub. No.: WO01/21089

PCT Pub. Date: Mar. 29, 2001

(30) Foreign Application Priority Data

Sep. 22, 1999 (FR) .............................................. 99 11837
May 10, 2000 (FR) .............................................. 00 05936
May 16, 2000 (FR) .............................................. 00 06233

(51) Int. Cl.⁷ ................................................. A61C 7/00
(52) U.S. Cl. ........................................ 433/9; 433/217.1
(58) Field of Search ............................ 433/9, 8, 200.1, 433/217.1; 29/896.1, 896.11

(56) References Cited

U.S. PATENT DOCUMENTS 6,048,205 A * 4/2000 Wright ..................... 433/202.1
6,299,438 B1 * 10/2001 Sahagian et al. .............. 433/6

* cited by examiner

*Primary Examiner*—Kevin Shaver
*Assistant Examiner*—Melba Bumgarner

(57) ABSTRACT

The invention concerns metallic orthodontic attachments, accessories and auxiliaries, new or recycled, surface treated with a platinum metal ion coating. But every metallic piece coming into direct contact with saliva is concerned by the invention. The deposits concern the whole surface of the metal coming into direct contact with saliva at least and are vapour deposited under vacuum or preferably by electroplating on an adhesive undercoat of fine gold. Said metal coats provide aesthetic and mechanical improvement with respect to prior art and above all medical improvement, since apart their discreet whiteness, close to that of teeth, they are reputable more noble than gold and can be implanted by surgery; they form a barrier to the allergenic nickel, cobalt and chromium ions and to toxic silver, tin, copper, aluminium and particularly cadmium ions sometimes alloyed in solders.

4 Claims, 1 Drawing Sheet

METAL ORTHODONTIC ATTACHMENTS TREATED WITH A COATING OF THE PLATINUM GROUP METAL

CROSS REFERENCE TO RELATED APPLICATION

This application is a continuation application of PCT Application No. PCT/FR00/02480 filed Sep. 8, 2000 which claims priority of French Application No. 00/05936 filed May 10, 2000, and No. 00/06233 filed May 16, 2000.

FIELD OF THE INVENTION

The invention relates to a coating applied on metallic orthodontic components; this coating, with a platinum group metal selected from the group of palladium, rhodium and platinum acts as a barrier to nickel allergen ions and is employed in the perfume and the jewellery industries. These metals are noble and surgically implantable. The components concerned are orthodontic attachments, their metal accessories and auxiliaries both new and recycled, as braces, hooks, bands, tubes, buttons, cleats, pins, springs, arch wires, arch bows, bumpers, expansions screws, quad-helix . . . this list being not exhaustive since every metallic piece coming into direct contact with saliva is concerned. The material used for these components is generally a nickel, chrome, cobalt or titanium alloy; they are industrially manufactured and available through specialist suppliers.

BACKGROUND OF THE INVENTION

It has been proposed at least as early as 1949 to subject metal dental products to a galvanoplasty platinum bath, as set forth in "Chimie des métaux et matériaux dentaires", Marcel Boll and Ch. Bennejeant," $3^{rd}$ Edition, J. B. Bailliere and Son, page 236. (1949) In the U.S. patent to Heligman U.S. Pat. No. 2,206,502, it was proposed to use a metal layer selected from the group of platinum as an intermediate layer joined with a ceramic powder layer. In the U.S. patent to Kato, et al., U.S. Pat. No. 4,780,079, it was proposed to coat a platinum group metal on an orthodontic fitting provided with an intermediate layer of cobalt, or layers cooper and nickel, so as to permit the cobalt positive ions to diffuse through it, thereby to act as a bactericide in the mouth.

In the Wood U.S. Pat. No. 5,882,193 a single layer from the group of platinum is deposed onto orthodontic fittings, thereby to facilitate the soldering of auxiliary components thereto, while affording a brighter and clearer appearance.

A previous technique consists too$_2$ in applying by electrolysis an 8 μms thickness 24 K gold layer on steel appliances, regardless of their shape. Another technique for depositing a metal layer is the so-called "Physical Vapor Deposition" -VPD- method, in which layers of titanium nitrides or zirconium are deposited on drills, saw milling cutters, watch cases, chrome automobile headlamps or loud speakers.

But a metal of the group of platinum does not attach well when directly applied on steel and a gold layer has to be applied with a minimum 8 μms thickness, because of its abrasion; which significantly alters the dimensions of a tight-fitting appliance.

SUMMARY OF THE INVENTION

One example of description is a brace.

This piece includes a base having a square section of about 10 square millimetres that is directly fastened to a tooth with a bonding resin or soldered on a band; the piece includes also a rectangular section slot, for retaining a metal arch wire that acts as a spring for straightening the tooth of the patient. A tube can replace the slot. The brace is cast, mould by injection, machined or assembled by soldering.

A "flash" 24 Kts. gold layer is deposited on the components in bulk; a palladium layer, then follows it.

As a primary variant of the invention, the designed for attachment base of the component that will be covered by the bonding resin in the mouth, remains untouched by any coating; so that its mechanical qualities remain unimpaired.

Or, a second variation of the invention is to obtain components with a base surface coated with 0.25 μm to 0.5 μm 24 carat gold, whereas the rest of the component, coming into contact with saliva is coated with a metal selected from the group of platinum, rhodium and platinum. The object of such an exercise is not merely aesthetic, since the component presents a yellow base and a shiny white surface, but also to load the components base as lightly as possible while providing the enamel a gold contact rather than a ferrous one: in these two cases a selected coating is practised.

This palladium coating is both: close to the natural appearance of teeth, harder than steel and sticks to the steel. By coating the orthodontic brasures, it moreover retains their silver, pewter, aluminium, copper and toxic cadmium ions. It has also a surgically implantable character.

BRIEF DESCRIPTION OF THE DRAWINGS

The brace chosen for the description is shown with.

Figure 1:
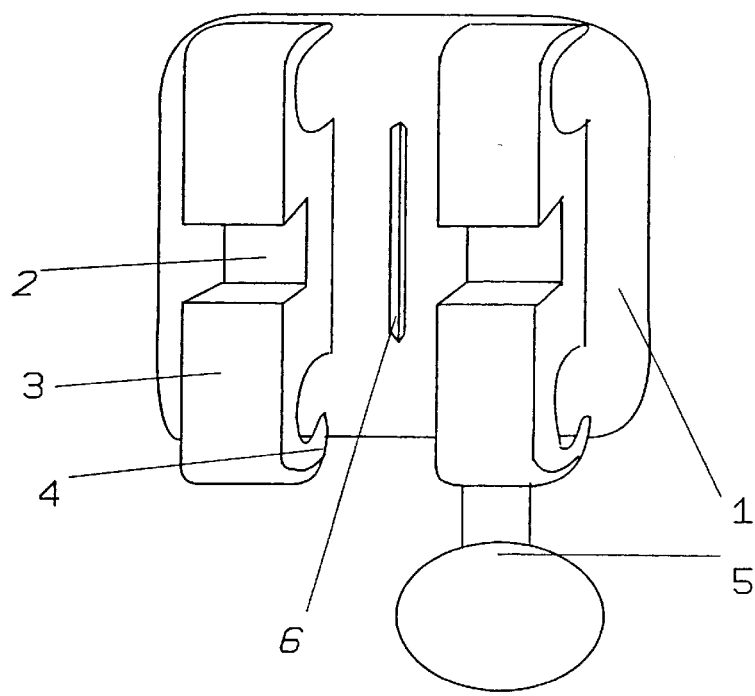
FIG. 1 Its front view
Figure 2:
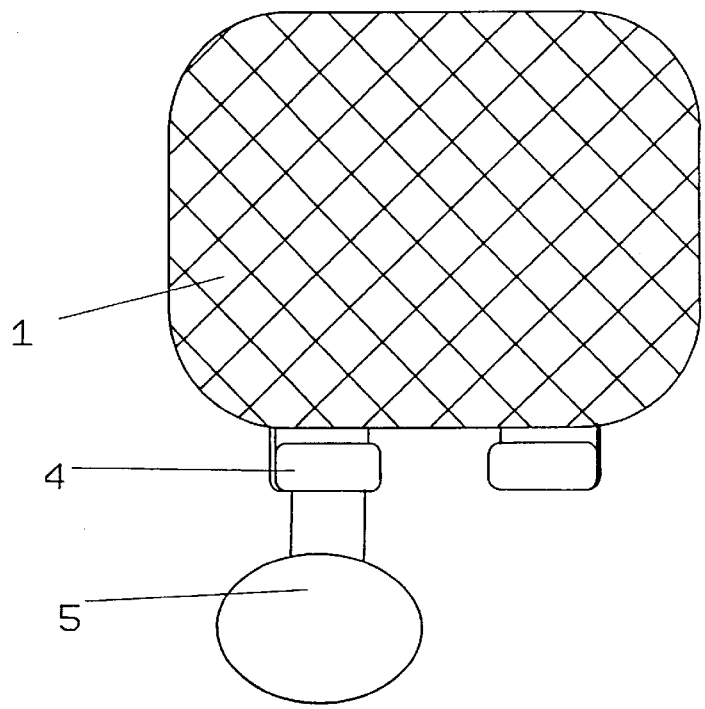
FIG. 2. Its base rear view

The front view shows the wings 3 containing the slot 2 for receiving the arch wire, the hooks 4 containing the ligature of the arch wire, an hook 5 anchoring an elastic of traction and a vertical guide mark 6.

The rear view shows the rear part of the base 1 that will be covered by the bonding resin.

DETAILED DESCRIPTION

In accordance with the preferred embodiment of the invention, the component is coated by electroplating, either in a still bath or preferably, in a barrel turning at a speed from 2 to 20 revolutions per minute. Since a metal selected from the group of platinum does not attach well to steel, an initial gilding is done first to provide a surface to which it can stick: to this end, a 0.25 μm "flash" deposit is achieved on the orthodontic components in bulk, the bath containing 2g of 24Kts gold per liter, at an intensity of 3 A/dm2.

After the initial bath is completed, a palladium layer is deposited with a coating thickness of about 1.3 μm, according to our method. The palladium bath contains 10 g palladium per liter at an intensity of 1 A/dm2.

Other parameters such as temperature and Ph must be considered, since only the time of exposure in the bath relative to the desired deposit thickness will vary.

In this manufacturing process, it is chosen palladium fixed by electroplating technique into barrel because of its ease of manufacture, reliability, chemical and mechanical qualities. The palladium bath may be replaced by another metal selected from the group of platinum provided that the parameters established by the supplier and the bath installer are met.

So, rhodium brings identical benefits to palladium, but is whiter, more glossy, three times harder (i.e., 800 HV hardness on Vickers scale) and is effective with a coating of 0.3 µm to 0.5 µm. Platinum is hard, but has a greyish tint and is less easily worked.

According to the first variant of the invention, the bonding base surface is first protected by an appropriate insulating prior to dipping in the first bath so as to prevent any electroplated ions from coating it. Alternatively, it can be chemically dissolved or it can be scraped clean by micro blast sanding after electroplating.

According to the second variant described above, the rear base is protected by an insulating prior to dipping in the second bath. An appropriate solvent removes the insulating after the component is passed to the second layer. At the end, the base remains yellow and the rest of the component is white.

Thus, this process can be extended to other orthodontic items whereby the interior part of a component such as a band, which comes into direct contact with a tooth, is as handled as the rear bonding base of a brace; as well as every metallic piece coming into direct contact with saliva is concerned.

With regard to TiN, the stoechiometric saturation of titanium by nitrogen must be optimal, so as to obviate any risk of potentially corrosive patches on the orthodontic pieces which will, besides, become discoloured. This in turn puts into question their effectiveness. Another pure metal might coexist in the bath of palladium, provided that the obtained deposit successfully passes the current tests of the allergenic ions detection.

While in accordance with the provisions of the patent statutes the preferred forms and embodiments of the invention have been illustrated and described, it will be apparent to those skilled in the art that various changes may be made without deviating from the inventive concepts set forth above.

What is claimed is:

1. An orthodontic device, comprising a metallic attachment with at least two successive nickel free, non-porous electroplated coatings; wherein the at least two coatings are on the whole surface of the attachment, wherein the at least two coatings include a 24 carat gold, underlayer followed by a noble layer of noble metal that is a minimum of 99.7% pure and selected from the group consisting of palladium, rhodium and platinum.

2. An orthodontic device as defined in claim 1, wherein said metallic attachment includes a metal selected from the group consisting of nickel, chromium, cobalt, titanium and titanium alloy; wherein said at least two coatings serve as a barrier to the allergenic, toxic ions emitted by said metallic attachment.

3. An orthodontic device as defined in claim 1 wherein said at least two coatings are applied by physical vapor deposition process.

4. A metallic orthodontic device, comprising a metallic component with at least two successive nickel free, non-porous electroplated coatings; wherein the at least two coatings are on the whole surface of the component, wherein the at least two coatings include a 24 carat gold underlayer followed by a noble layer of noble metal that is a minimum of 99.7% pure and selected from the group consisting of palladium, rhodium and platinum.

* * * * *